United States Patent [19]

Blumberg

[11] Patent Number: 5,021,450

[45] Date of Patent: Jun. 4, 1991

[54] CLASS OF COMPOUNDS HAVING A VARIABLE SPECTRUM OF ACTIVITIES FOR CAPSAICIN-LIKE RESPONSES, COMPOSITIONS AND USES THEREOF

[75] Inventor: Peter M. Blumberg, Frederick, Md.

[73] Assignee: The United States of America as represented by the Secretary of the Department of Health and Human Services, Washington, D.C.

[21] Appl. No.: 358,073

[22] Filed: May 30, 1989

[51] Int. Cl.$^5$ .................... A61K 31/35; A61K 31/12; C07D 311/78; C07C 69/76

[52] U.S. Cl. .................................. 514/453; 514/691; 549/381; 549/382; 560/75

[58] Field of Search ................ 549/381, 382; 514/453, 514/533, 691; 560/75

[56] References Cited

PUBLICATIONS

Adolf et al, Journal of Natural Products, vol. 45, No. 3, 1982, pp. 347–354.
Hergenhahn et al, Tetrahedron Letters, No. 19, pp. 1595–1598 (1975).
Driedger et al, Proc. Natl. Acad. Sci., U.S.A., vol. 77, No. 1, pp. 567–571 (1980).
Hendricks et al, Proc. Natl. Acad. Sci., U.S.A., vol. 76, No. 2, pp. 778–781 (1979).
Driedger et al, Cancer Research 40, 1400–1404 (1980).
Hergenhahn et al, Carcinogensis, vol. 2, No. 12, pp. 1277–1281 (1981).
Geppetti, et al, Bri. J. Pharmacology, vol. 93, p. 509 (1988).
Schmidt et al, Phytochemistry, vol. 15, p. 1778 (1976).
Hayes et al, *Life Sciences*, 34, pp. 1241–1248 (1984).
Newman, *Chemical Products*, Mar. 1954, pp. 102–106.

*Primary Examiner*—Cecilia Shen
*Attorney, Agent, or Firm*—Birch, Stewart, Kolasch & Birch

[57] ABSTRACT

The present invention relates to a new class of compounds having a variable spectrum of activities for capsaicin-like responses, compositions thereof, processes for preparing the same, and uses thereof. Compounds of the invention are prepared by combining phorbol related diterpenses and homovanillac acid analogs via esterification at the exocyclic hydroxy group of the diterpene. Examples of these compounds include 20-homovanillyl-mezerein and 20-homovanillyl-12-deoxyphorbol-13-phenylacetate.

18 Claims, 1 Drawing Sheet

FIG. 1

CLASS OF COMPOUNDS HAVING A VARIABLE SPECTRUM OF ACTIVITIES FOR CAPSAICIN-LIKE RESPONSES, COMPOSITIONS AND USES THEREOF

CROSS-REFERENCE TO RELATED APPLICATION

This is a continuation-in-part application of application U.S. Ser. No. 07/261,627 filed on Oct. 24, 1988, U.S. Pat. No. 4,939,149, which is herein incorporated by reference.

BACKGROUND OF THE INVENTION

1. Field of the Invention

The present invention relates to a new class of compounds having a variable spectrum of activities for capsaicin-like responses, compositions thereof, processes for preparing the same, and uses thereof.

2. Description of Related Art

Resiniferatoxin (RTX) is an extremely irritant diterpene present in the latex of several members of the genus Euphorbia (Hergenhahn et al., *Tetrahedredron Lett.*, Vol. 19, p. 1595 (1975); Schmidt et al., *Phytochemistry*, Vol. 15, p. 1778 (1976)). It was isolated based on its extraordinary activity in the mouse ear erythema assay (Hergenhahn et al., *Tetrahedron Lett.*, Vol. 19, p. 1595 (1975)) in which it was found to be 1000-fold more potent than the most active of the typical phorbol esters, phorbol 12-myristate 13-acetate (Hecker, *Carcinogenesis*, Vol. 2, p. 11, Raven Press, New York (1978); Adolph et al., *J. Nat. Prod.*, Vol. 45, p. 347 (1982)). Except for its irritancy, RTX failed to induce typical phorbol ester effects (e.g. promoting activity or activation of EB virus (zur Hausen et al., *Proc. Natl. Acad. Sci. USA*, Vol. 76, p. 782 (1979)), release of fibronectin (Driedger et al., *Cancer Res.*, Vol. 40, p. 1400 (1980a)), competition for phorbol ester binding to protein kinase C (Driedger et al., *Proc. Natl. Acad. Sci. USA*, Vol. 77, p. 567 (1980b)), indicating that it exerted its irritancy via a different pathway.

RTX differs from those resiniferonol derivatives which are tumor promoting in that it is esterified with homovanillic acid at the C20 position. Structure-activity analysis had indicated that this substituent is critical for its acute irritant activity (Adolph et al., *J. Nat. Prod.*, Vol. 45, p. 347 (1982); Schmidt et al., *Inflammation*, Vol. 3, p. 273 (1979)), whereas a free C20 hydroxyl is required for the promoting activity of typical phorbol esters (Hecker, *Carcinogenesis*, Vol. 2, p. 11, Raven Press, New York (1978)). Strikingly, a homovanillyl substituent also plays an essential role in determining the pungency of capsaicin, the major irritant constituent in red pepper and other species of the genus Capsicum (Jancso, *Pharmacology of Pain*, Vol. 9, p. 33, Permamon Press, Oxford (1968); Szolcsanyi and Jancso-Gabor, *Arzneim.-Forsch. (Drug Res.)*, Vol. 25, p. 1877 (1975)).

Recently, it has been demonstrated that RTX acts as an ultrapotent analog of capsaicin (Szallasi et al., *Neuroscience* (in press, 1989); RTX excites and then desensitizes polymodal nociceptor neurons. These sensory neurons are located in the dorsal root and Gasser ganglia. They transmit perception of pain to the central nervous system and mediate the release of inflammatory neurotransmitters (e.g. substance P) in the periphery (Buck et al., *Pharmacol. Rev.*, Vol. 38, p. 179 (1986)). RTX was 3-4 orders of magnitude more potent compared to capsaicin, the most active known congener of its class (Szallasi et al., *Neuroscience* (in press, 1989)).

These results raised the possibility that other 20-homovanillyl esters of diterpenes might also be potent sensory neuromodulator agents. Given the renewed interest in the mechanism of action of capsaicin (Marsch et al., *Neuroscience*, Vol. 23, p. 275 (1987); Wood et al., *J. Neuroscience*, Vol. 8, p. 3208 (1988)) and its possible therapeutical implications (Geppetti et al., *Br. J. Pharmacol.*, Vol. 93, p. 509 (1988); Levine et al., *J. Neuroscience*, Vol. 6, p. 3423 (1986)), the structure-activity analysis of such diterpenes might provide useful information on the requirements for interaction at the postulated capsaicin receptor (Szolcsanyi and Jancso-Gabor, *Arzneim.-Forsch. (Drug Res.)*, Vol. 25, p. 1877 (1975)). Moreover, the compounds might provide further tools for dissecting subclasses of capsaicin responses, as was strongly implied by the differential activity of RTX (Szallasi et al., *Neuroscience* (in press, 1989)).

In the present study, the potencies of two homovanillyl diterpene derivatives of the new class of claimed compounds are examined, 12-deoxyphorbol 13-phenylacetate 20-homovanillate and mezerein 20-homovanillate for mimicking RTX. The structure of resiniferatoxin and its analogs along with Tinyatoxin are shown below.

Resiniferatoxin

-continued 20-homovanillyl-mezerein 20-homovanillyl-12-deoxyphorbol 13-phenylacetate Tinyatoxin

Activities are compared with those for the parent diterpenes, and all compounds are also examined to determine their binding affinities for protein kinase C.

SUMMARY OF THE INVENTION

The present invention relates to a new class of compounds having a variable spectrum of activities for capsaicin-like responses which are represented by formulas (I)–(IV):

-continued wherein $R_1$ in all cases represents to yield 20-homovanillyl esters of diterpenes of the tigliane (I), daphnane (II and III), and ingenane (IV) classes.

Specific substitutions are as follows:

I

-continued

II wherein at least one of R', R" or R''' are aromatic and the remainder are $(CH_2)_{n'}CH_3$ wherein n' is 0-14. For instance, the aromatic group may be

III wherein $R_6$-$R_{10}$ each independently may represent OH, $OCH_3$ or H and wherein n is 0-10. Preferably, the aromatic group is (wherein n = 0-10)

IV

II and III:
R' is aromatic as defined above;
$R_3$ is H, OH or where R" is aromatic as defined above,
$R_4$ is H or where R''' is aromatic as defined above.
IV:
$R_2=$ $R_3=CH_3$ or $R_4=$H or $$\overset{\text{O}}{\underset{}{\text{CR'''}}}$$

where R', R", or R''', is aromatic as defined above. However, RTX and TTX are not encompassed by the new class of compounds represented by formulas (I)–(IV).

Representative examples of compounds of formulas (I)–(IV) include 20-homovanillyl-mezerein and 20-homovanillyl-12-deoxyphorbol-13-phenylacetate.

The invention is further directed to compounds produced by the process of reacting phorbol-related diterpenes and homovanillic acid by esterification at the exocyclic hydroxy group of the diterpene.

Moreover, the invention is directed to a method for desensitizing a subject animal, which comprises administering to the subject animal a therapeutically effective desensitizing amount of a compound produced by esterification of phorbol-related diterpenes and homovanillic acid analogs for desensitizing the subject to neurogenic inflammation, to chemically and thermally induced pain, to responses involving sensory afferent pathways sensitive to capsaicin and to responses involving the hypothalamic temperature control region, and a pharmaceutically acceptable carrier therefor.

The invention is further directed to pharmaceutical compositions containing these compounds.

DETAILED DESCRIPTION OF THE INVENTION

Capsaicin stimulates and then desensitizes sensory afferent C-fibers and the hypothalamic temperature control region. The induced desensitization may have application in arthritis, asthma, allergic responses including rhinitis, fever, pain, including pain associated with cancer and postherpetic neuralgia, and in biological processes mediated by tachykinins, including substance P. This application describes compounds with a variable spectrum of activities for capsaicin-like responses, compositions thereof, processes for producing these compounds and uses thereof.

A new class of compounds having capsaicin-like responses are represented by formulas (I)–(IV) as defined above.

Resiniferatoxin (RTX), unlike the structurally related phorbol esters, acts as an ultrapotent analog of capsaicin, the pungent principle of the red pepper. A homovanillyl group is an essential structural feature of capsaicin and the most prominent feature distinguishing resiniferatoxin from typical phorbol-related compounds. Representative examples of compounds of formula (I) having RTX-like activity include two 20-homovanillyl esters of diterpene derivatives with particular similarities to RTX. The potency of 12-deoxyphorbol 13-phenylacetate 20-homovanillate (dPP-HV) is comparable to RTX for local induction and desensitization of chemical pain but is 2-4 orders of magnitude less potent for the other RTX responses tested (e.g. stimulation and desensitization of neurogenic inflammation and hypothermia). Mezerein 20-homovanillate (Mez-HV) displays very weak activity in pain induction and is inactive in the other assays. The parent derivatives—resiniferonol orthophenylacetate, 12-deoxyphorbol 13-phenylacetate and mezerein—are inactive in inducing RTX-like effects. Reciprocally, the presence of the 20-homovanillate ester reduced binding affinities to protein kinase C by 11-, 130-, and 690-fold for RTX, dPP-HV, and Mez-HV, respectively. These findings provide further evidence for heterogeneity among capsaicin-sensitive pathways.

Furthermore, esterification of phorbol-related diterpenes with homovanillic acid can yield capsaicin analogs with unique activities. Accordingly, the invention is directed to compounds produced by the process of reacting phorbol-related diterpenes and homovanillic acid by esterification at the exocyclic hydroxy group of the diterpene. Representative examples of the phorbol-containing diterpenes are:

$R = OC(CH=CH)_2C_6H_5$
Mezerein $R_1 = COCH_2C_6H_5$
$R_2 = H$
12-deoxyphorbol 13-phenylacetate The phorbol related diterpenes may be selected from the group consisting of tiglianes, daphnanes or ingenanes.

Representative examples of homovanillic acid and congeners are:

Homovanillic acid itself or congeners possessing a pattern of substitution which would confer capsaicin-like activity were it in a capsaicin-like structure may also be used.

The compounds of the invention, RTX and Tinyatoxin may be prepared using the methodology for esterification as set forth in *J. Natural Prod.* Vol. 45, p. 348 (1982).

The inventor has confirmed the possible homology of RTX and capsaicin (i.e. both compounds produced a dramatic fall in body temperature in mice followed by cross-tolerance (deVries et al (1988) submitted, Life Sciences) and has now compared the potencies and in vivo activities of RTX, dPP-HV, Mez-HV and capsaicin in detail, as discussed herein below.

Accordingly, the inventor has characterized a new class of compounds having capsaicin-like activity. Moreover, RTX qualitatively resembles capsaicin in its activity, but differs quantitatively in potency (i.e. $10^3$–$10^4$ fold more potent) and in relative spectrum of actions. Resiniferatoxin, tinyatoxin (TTX) and the novel compounds of the invention thus cause desensitization of neurogenic inflammation, to chemically and thermally induced pain, and to responses involving sensory afferent pathways including C-fibers and the hypothalamic temperature control region. The induced desensitization may have application to arthritis, asthma, allergic responses, fever, pain associated with cancer or Herpes virus infection, and in biological processes mediated by substance P or other neuropeptides depleted by capsaicin treatment.

As indicated above, resiniferatoxin has similar effects to capsaicin, but differs in its much greater potency—up to $10^4$, which should remarkably reduce side effects and permit easier application (i.e. smaller volume or absorption through inefficient routes). RTX, TTX and the compounds of the invention also show a somewhat different spectrum of action, enabling greater desensitization at a given level of systemic toxicity and greater desensitization relative to acute induction of pain.

Moreover, desensitization by resiniferatoxin, TTX and the compounds of the invention can be activated by topical, intravenous, intraperitoneal, oral, and subcutaneous administration. RTX, TTX and the compounds of the invention may be administered to a domestic animal or to an animal such as a mammal (e.g. mouse, rat or human).

Furthermore, it should be noted that capsaicin exerts its actions on all mammals examined, but not on birds and lower vertebrates (Monsereenusorn et al. (1982) *CRC Crit. Rev. Toxicol.* Vol. 10, p. 321-339). Based on the resemblances in the activities of capsaicin, resiniferatoxin, TTX and the compounds of the invention documented in this application, it is extrapolated that the effects of RTX are not limited to rats and mice but extend to man as well.

RTX, TTX and the compounds of the present invention can be made into pharmaceutical compositions by combination with appropriate medical carriers or diluents. For example, RTX, TTX or the compounds of the present invention, can be dissolved in oils, propyleneglycol or other solvents commonly used to prepare injectable solutions. Suitable carriers include physiological saline, polyethylene glycol, ethanol, sesame oil, cremophor and isopropyl myristate. For topical application, RTX, TTX or the compounds of the invention can be formulated as an ointment or cream.

The following methods and excipients are merely exemplary and in no way limit the invention.

The compounds of the present invention (including RTX and TTX) in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, Dextrose 5%, or nonaqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the invention may be combined with other compounds having the desired effect.

The desirable dose of the compounds of the present invention varies with the subject, drug form, method and period of administration. However, in order to obtain desirable effects, generally it is recommended to administer $0.1\times10^{31}$ 3 to 10 mg/kg, preferably $0.1\times10^{-3}$ to 0.1 mg/kg, body weight of the compounds of the present invention for single application, or less upon multiple application. The compounds of the invention may also be administered in the range of $1\times10^{-5}$ mg/kg to 10 mg/kg to the subject. In terms of composition, compounds should be present between 0.0001 to 10% by weight, preferably 0.0001 to 1% by weight.

The following Examples are intended to illustrate the claimed invention and will enable others skilled in the art to understand the invention more completely. However, the invention should not be interpreted as being limited to only these representative examples.

EXAMPLE 1

Representative Protocol 50 micromoles of homovanillic acid in ethanol is evaporated to dryness under $N_2$, is three times re-dissolved in acetonitrile and evaporated to dryness to remove traces of ethanol.

The diterpene ester, e.g. 12-deoxyphorbol 13-phenylacetate (50 micromoles) is dissolved in anhydrous pyridine and evaporated to dryness three times. N-methylfluoropyridinium tosylate (25 mg) is added, plus 0.25 ml of a solution of methylene chloride (5 mL, distilled from $P_2O_5$) and 0.14 ml of triethylamine (distilled from phenyl isocyanate). After one half hour the mixture is evaporated to dryness, the flask is covered with a septum, flushed with $N_2$, and 0.25 ml of a solution of benzene (2 ml, distilled from Na) and triethylamine (0.17 ml) is added, followed by the homovanillic acid in 0.25 ml of acetone (dried over molecular sieves). After stirring 1.5 hours at 60° C., the mixture is taken up in phosphate buffer (pH 7.5) and extracted 5x with ethyl acetate.

The combined extracts are dried over $Na_2SO_4$, filtered, and evaporated. The dried extract is chromatographed on a $SiO_2$ column. The first fraction ($Et_2O$-hexane, 4:1) is evaporated and the residue injected into a Magnum-C18 HPLC column (70% $MeOH$—$H_2O$). The product peak is collected and the solvent removed.

EXAMPLE 2

20-Homovanillic-12-deoxyphorbol 13-phenylacetate (dPP-HV)

Homovanillic acid (1 g, 0.003 M) and dicyclohexylcarbodiimide (DCC) (0.3 g, 0.0015 M) were stirred one hour in 20 ml of $CH_3CN$—$CH_2Cl_2$ (1:1). The solution was filtered, evaporated, dissolved in ethyl acetate and again filtered. After evaporation the residue was dissolved in a few ml of benzene and left overnight. The crystals were filtered. mp 111°–114°.

The above homovanillic anhydride (60 mg, excess) was stirred in anh. pyridine (5 ml) with 12-deoxy-phorbol 13-phenylacetate (25 mg) overnight. The solvent was evaporated and the residue was dissolved in ethyl acetate, washed twice with aq. citric acid, then with aqueous sodium bicarbonate, dried over sodium sulfate, filtered and evaporated. Chromatography on $SiO_2$ eluted a very small amount of material with chloroform, then a large amount of material with 3% $CH_3OH$—$CHCl_3$, which by mass spectroscopy appeared to be starting material. All fractions were recombined, dried by repeated evaporation of pyridine and resubmitted to reaction with the acyl anhydride as above, except a small amount of DMAP (dimethylaminopyridine) was added and the reaction time was two days. After workup and chromatography as above, a considerable amount of unreacted starting material was again isolated, which was again re-submitted to reaction for four days. After workup and chromatographic isolation of the product-bearing fraction, all crude products were combined and purified by preparative HPLC on a magnum C-18 column, eluting with 70% MeOH—$H_2O$. The major peak was collected after 5.3 min. at 50 ml/min. Evaporation yielded 14 mg of product which appears good by mass spectrometry and NMR.

The reaction scheme is represented as follows:

12-Deoxyphorbol-13-Phenylacetate $\xrightarrow[\text{DMAP}]{\text{Pyridine}}$ dPP-HV

EXAMPLE 3

Preparation of Mezerein Homovanillate (Mez-HV)

Homovanillic acid (0.618 g, -.0034M) and dicyclohexylcarbodiimide (0.385 g, 0.0019 M) were stirred in 20 ml $CH_3CN$—$CH_2Cl_2$ (1:1) overnight. The solution was filtered and evaporated to yield an oil which was triturated with ether-hexane. The supernatant was evaporated, treated with ether-hexane and chilled to yield a solid, mp 100°–105° C. The NMR shows the material to contain 5–10% of an impurity which could not be removed by recrystallization. The impurity is probably a self-esterification product of homovanillic anhydride and/or acid. To prevent this side reaction would require blocking the phenolic OH group, but we were unable to find a blocking group which could be removed without cleaving the desired ester.

In order to prepare mezerein homovanillate, mezerein (30 mg, 0.046mm) and homovanillyl anhydride (15.9 mg, 0.046 mm) were stirred in CaH-dried $CH_2Cl_2$ (approx. 3 ml) with 1 drop pyridine and a small amount of dimethylaminopyridine for 3 days. The solution was diluted with chloroform, washed with aqueous citric acid, then with aqueous bicarbonate and dried over $Na_2SO_4$. Evaporation yielded a glass which still contained unreacted mezerein by HPLC. The product was isolated by preparative HPLC on a magnum $SiO_2$, column (Whatman Partisil 10 mq/25) using 1.5% MeOH in $CHCl_3$. The first peak was collected. The second peak was mezerein. The product appears pure by normal phase HPLC, but contains an impurity by reverse phase HPLC, probably resulting from the impurity in the homovanillyl anhydride. Preparative thin-layer chromatography ($SiO_2$) using 10% 2-$C_3H_7OH$-90% $C_6H_6$ failed to remove the impurity. Finally, the product was purified by HPLC on an ALTEX ODS column (25 cm×10 mm) using 85% MeOH-$H_2O$ (3 ml/min.). The major peak eluting at 12 min. was collected. Evaporation yielded 2.2 mg of a glass. Mass spectroscopy (FAB+) shows the correct molecular ion peak and NMR shows the presence of one homonvanillyl moiety.

The reaction of Example 3 is shown below:

EXAMPLE 4

Materials and Methods

RTX and resiniferonol 9,13,14-orthophenylacetate were purchased from Chemsyn Science Laboratories (Lenexa, Kans.). Mezerein, phorbol 12,13-dibutyrate (PDBu), and phosphatidylserine were obtained from Sigma (St. Louis, Mo.). The dPP was from LC Services (Woburn, Mass.). dPP-HV and Mez-HV were synthesized by the Chemical Synthesis and Analysis Laboratory, NCI-FCRF, Frederick, Md. [$^3$H]PDBu (20 ci/mmol) was from New England Nuclear (Boston, Mass.).

In vivo experiments were performed on Sprague-Dawley rats (females, 250–300 g). Pain response was measured in the eye-wiping test (Jancso et al., *Acta Physiol. Acad. Sci. Hung.*, Vol. 19, p. 113 (1961)); increasing concentrations of the compounds were instilled into the eyes of the rats and the number of protective wiping movements with the forelegs counted. Solutions were made up in 10% ethanol, 10% Tween-80, 80% physiological saline. The solvent containing 10% ethanol induced no wipings by itself. When the concentration of ethanol in the solvent was increased to 20%, it was found to be slightly active in provoking wiping movements which were then subtracted from the number of protective wipings elicited by the respective compounds. Relative pain-producing potencies (RPP) were calculated based on the concentrations inducing an equal response of 10 wipings if the potency of RTX was taken as 1000 (Szolcsanyi and Jancso-Gabor. *Arzneim.-Forsch. (Drug. Res.)*, Vol. 25, p. 1877 (1975)). To minimize discomfort, complete dose response curves were not performed.

Local desensitization against a chemically-induced pain response was examined by dropping an irritant concentration (1%) of capsaicin into the eyes of rats 2 hr after instillation of the tested compound (Jancso et al., *Acta Physiol. Acad. Sci. Hung*, Vol. 19, p. 113 (1961)). The degree of desensitization was calculated from the number of wipings induced by capsaicin in control and pretreated rats.

al., *Br. J. Pharmacol. Chemother.*, Vol. 31, p. 138 (1967)) in control and pretreated rats. Systemic desensitization was examined 6 hr after administration of the test compound.

Inhibition of [³H]PDBu binding to protein kinase C was determined as described previously (Sharkey et al., *Cancer Res.*, Vol. 45, p. 19 (1985)), but using protein kinase C purified through the DEAE-cellulose chromatography step (Jeng et al., *Cancer Res.*, Vol. 46, p. 1966 (1986)).

Results

Figure 1:
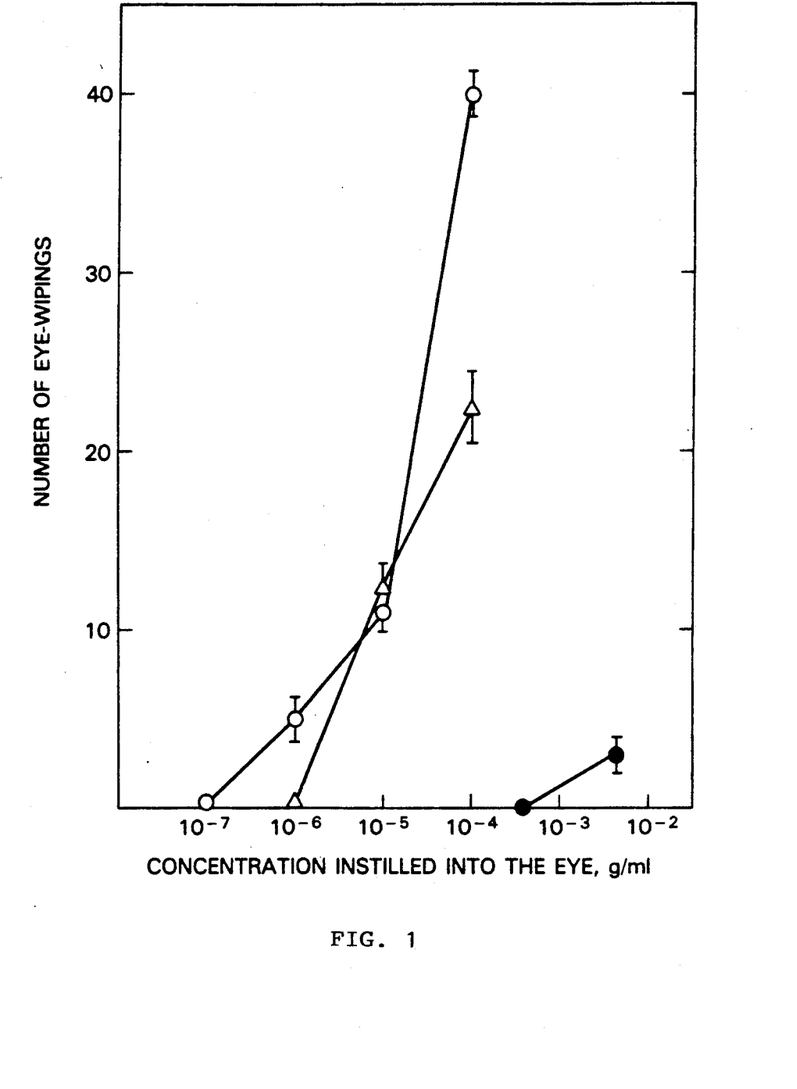
FIG. 1 shows the dose dependence of eye wipings in response to instillation of RTX.

The eye-wiping assay permits the evaluation of the potencies at polymodal nociceptors of compounds available in only limited amounts. RTX and dPP-HV displayed comparable activity in this assay (see FIG. 1). In FIG. 1, the compounds tested are represented as follows: RTX (○), dPP-HV (△), and Mez-HV (●). Each value is the mean ±SEM for 10–15 animals in 2–3 experiments. In contrast, Mez-HV was approximately 4 orders of magnitude less potent, and the corresponding parent compounds showed no activity up to the highest concentrations permitted by their solubilities ($1-5 \times 10^{-3}$ g/ml). The RTX-induced eye-wiping movements started 5–10 sec after instillation as reported earlier (Szallasi et al., *Neuroscience* (in press, 1989)); the delay following dPP-HV instillation was longer (20–30 sec). The relative pain-producing potencies (RPP) of these compounds are summarized in Table I.

TABLE I

| Compound | RPP[1] | Local desensitization against neurogenic pain | | Systemic desensitization against | | | | Neurogenic inflammation | |
|---|---|---|---|---|---|---|---|---|---|
| | | | | neurogenic pain | | inflammation | | | |
| | | conc. g/ml | inhibition % | dose ug/kg | inhibition % | dose ug/kg | inhibition % | dose ug/paw | Evan's blue ng/mg tissue |
| RTX | 1000 | $10^{-4}$ | 43 | 10 | 100 | 300 | 100 | 100 | 91.6 ± 3.6 |
| ROA[2] | 1 | $10^{-3}$ | 0 | 300 | 0 | 300 | 0 | 100 | 0 |
| Mez-HV | 0.1 | $10^{-3}$ | 0 | 300 | 0 | 300 | 0 | 100 | 0 |
| Mez | 0.1 | $10^{-3}$ | 0 | NT[3] | | 300 | 0 | 250 | 0 |
| dPP-HV | 1000 | $10^{-3}$ | 78 | 300 | 19 | 300 | 26 | 100 | 0 |
| | | | | | | 1000 | 62 | | |
| dPP | 1 | $10^{-3}$ | 0 | NT[3] | | 300 | 0 | 100 | 0 |

[1] RPP = Relative Pain-Producing Potency
[2] ROA = Resiniferonol 9,13,14-Orthophenylacetate
[3] NT = Not Tested Neurogenic pain response was induced by 1% capsaicin solution dropped into the eyes of rats; neurogenic inflammatory response was induced by applying xylene (50 ul) to the hind paw and quantitated by measuring Evan's blue extravasation.

Inflammatory response was quantitated by measuring Evan's blue extravasation induced by topical application of the tested compound (Saria et al., *J. Neurosci. Meth.*, Vol. 8, p. 141 (1983)). A 1% Evan's blue solution (20 mg/kg made up in physiological saline containing 100 IU/ml heparin) was injected intravenously under deep ether anesthesia, then 5 min later 50 ul of compounds dissolved in acetone were applied topically to the hind paw. 30 min later, the time point of maximal RTX-induced Evan's blue extravasation (Szallasi et al., *Neuroscience* (in press, 1989)), the rats were sacrificed; the hind paw skin was removed and quickly weighed. Extravasated Evan's blue was extracted from tissues by overnight incubation in hot (50° C.) formamide and then measured spectrophotometrically at 620 nm.

In order to investigate systemic desensitization, compounds were injected subcutaneously in the above mentioned solvent. Desensitization of the chemically-induced pain response was determined as described above. Desensitization against neurogenic inflammation was determined by comparing Evan's blue extravasation in response to topically applied xylene (Jancso et The second response examined that is mediated by polymodal nociceptors is stimulation of neurogenic inflammation. Neurogenic inflammation can be quantitated by measuring Evan's blue extravasation (Jancso et al., *Br. J. Pharmacol. Chemother.*, Vol. 31, p. 138 (1967); Saria et al., *J. Neurosci. Meth.*, Vol. 8, p. 41 (1983)). In the case of topical RTX treatment Evan's blue extravasation reaches its peak value 30 min after application (Szallasi et al, *Neuroscience* (in press, 1989)). No extravasation was seen for dPP-HV, for Mez-HV, or for the parent diterpenes over this time period (see Table I).

If the observation period was increased to 3 hrs, slight extravasation was observed for mezerein and dPP treatment. In these experiments, RTX, dPP-HV, and Mez-HV were employed at equal doses. Because of limited quantities of the latter two compounds, activities at higher doses could not be evaluated. Nonetheless, since RTX at $3 \times 10^{-6}$ g/paw gives a detectable response (Szallasi et al., *Neuroscience*, (in press, 1989)), our results suggest that both dPP-HV and Mez-HV are at least 30-fold less potent than RTX for this response.

A unique feature of capsaicin congeners is that they, unlike other neurogenic irritants, desensitize the polymodal nociceptors after the initial stimulatory phase (Jancso, 1968). Both local and systemic desensitization of the chemically-induced pain response and systemic desensitization of the neurogenic inflammatory pathway were examined. Like RTX, dPP-HV was able to desensitize to chemically-induced pain and to neurogenic inflammation (see Table I above). For desensitization of pain upon local administration, dPP-HV was within 10-fold of RTX in potency. Its relative effectiveness in systemic desensitization was less. Based on dose-response curves for RTX obtained in previous experiments (Szallasi et al., Neuroscience, (in press, 1989)), the relative potency of dPP-HV for desensitizing to chemically induced pain was approximately 3000-fold less, and for inhibiting xylene-induced Evan's blue extravasation was 300-fold less (see Table I above). The amounts of dPP-HV available prevented more extensive analysis. No activity was found for Mez-HV or the parent diterpenes.

Induction of hypothermia is a third typical response of capsaicin congeners (Szolcsanyi, Handbook of Experimental Pharmacology, p. 437 (1982)). For further comparison of biological activity, the relative potencies of RTX and dPP-HV for induction of hypothermia was also investigated. Systemic administration of dPP-HV at a dose of 1000 ug/kg, a dose higher than the ED50 for desensitization against neurogenic inflammation, was totally inactive in inducing hypothermia. dPP-HV was thus at least 4 orders of magnitude less potent for this response than RTX, which produces a substantial drop in body temperature at a dose as low as $10^{-7}$ g/kg (Szallasi et al., Neuroscience, (in press, 1989)). Although the amount of dPP-HV sufficed for treating only 4 rats in the hypothermia experiment, the result is of importance because it provides further evidence for the heterogeneity in response to different capsaicin congeners.

The receptor for phorbol esters and related diterpenes is the $Ca^{2+}$, phospholipid-dependent protein kinase, protein kinase C (Nishizuka, Nature, Vol. 308, p. 693 (1984)). Since a free 20-hydroxyl group on the phorbol esters is important for activity, it is believed that the 20-homovanillate group on dPP-HV and Mez-HV would reduce their affinities for protein kinase C at the same time that it increases their activities as capsaicin analogs. Binding affinities were measured by competition of [$^3$H]phorbol 12,13-dibutyrate binding. For each of the 3 pairs of compounds examined, esterification with homovanillic acid reduced protein kinase C binding affinity as expected. The extent of the reduction of affinity depended substantially on the nature of the diterpene esters. It ranged from 11-fold for RTX to 690-fold for Mez-HV. The absolute affinities for all these homovanillyl esters were between 80 and 400 nM, compared to 0.6 nM for phorbol 12,13-dibutyrate (see Table II below).

TABLE II

| Compound | Binding Affinities to Protein Kinase C | |
|---|---|---|
|  | $K_I$ (nM) | Relative Affinity |
| RTX | 404 ± 63 (n = 5) | 11 |
| Resiniferonol 9,13,14-orthophenylacetate | 36 ± 9 (n = 2) |  |
| Mez-HV | 400 ± 110 (n = 3) | 690 |

TABLE II-continued

| Compound | Binding Affinities to Protein Kinase C | |
|---|---|---|
|  | $K_I$ (nM) | Relative Affinity |
| Mez | 0.58 ± 0.06* (n = 3) |  |
| dPP-HV | 82 ± 13 (n = 2) | 130 |
| dPP | 0.64 ± 0.01 (n = 3) |  |

*From Sharkey, N.A., Hennings, H.H., Yuspa, S.H. and Blumberg, P.M., Carcinogenesis (submitted).

Discussion

The structure-activity analysis of capsaicin congeners has been the object of intensive study for almost 6 decades. Initial interest was generated by the search for synthetic pepper-flavored substances (Newman, Chem. Prod. Chem. News. (London), Vol. 27, p. 467 (1953)). Since the discovery that capsaicin had a peculiar pharmacological effect on sensory neurons—after initial stimulation it exerted the opposite action, i.e. it induced desensitization (Jancso, Pharmacology of Pain, Vol. 9, p. 33, Pergamon Press, (1968))—structure-activity analysis has also been extended to structural differences between capsaicin congeners with high and low desensitization activity. Initial findings suggested that the acylamide type linkage was essential for desensitization (Jancso, Pharmacology of Pain, Vol. 9, p. 33, Pergamon Press, (1968)). Further, more detailed studies on capsaicinoids indicated that the ester linkage, as is found in RTX, was adequately tolerated in place of the acylamide linkage (Szolcsanyi et al., Arzneim.-Forsch. (Drug. Res), Vol. 25, p. 1877 (1975)). It was also found that, although the homovanillyl group was essential for activity, some capsaicin-analogs possessing this substituent were inactive (Szolcsanyi et al., Arzneim.-Forsch. (Drug Res.), Vol. 25, p. 1877, (1975)).

The basic mechanism by which capsaicin—unlike other pungent agents acting on sensory neurons—desensitize these nociceptors is still unknown. In vivo morphological (Jancso et al., Brain Res., Vol. 295, p. 211 (1984)) and in vitro neurophysiological (Marsh et al., Neuroscience, Vol. 23, p. 275 (1987)) or neurochemical (Wood et al., J. Neurosci., Vol. 8, p. 3208 (1988)) investigations strongly argued for the role of calcium uptake through non-conventional capsaicin-sensitive cation channels. This intracellular calcium accumulation might account for the neurodegeneration observed in newborn animals or the long-lasting desensitization in adult animals (Buck et al., Pharmacol. Rev., Vol. 38, p. 179 (1986)). Recently we have shown that RTX, a diterpene esterified with a homovanillyl substituent at the C20 position, acts like an ultrapotent capsaicin analog (Szallasi et al., Neuroscience (in press, 1989)). These results suggest that homovanillyl-diterpenes might represent a new class of capsaicin congeners.

Resiniferonol 9,13,14-orthophenylacetate, the parent compound of RTX was found to be totally inactive for the biological responses characteristic of RTX. Our evidence that it is at least 1000-fold less potent than RTX is in good agreement with its relative potency in the mouse ear erythema assay (Schmidt et al., Inflammation, Vol. 3, p. 273 (1979)). Likewise, resiniferonol 9,13,14-orthophenylacetate was 100-fold less active in competing for phorbol esters binding sites on protein kinase C than was dPP or mezerein. Its potency in the ear reddening assay had been reported to be 25-fold and 33-fold less than that of dPP and mezerein, respectively, likewise in good agreement (Hergenhahn et al., J. Cancer Res. Clin. Oncol., Vol. 104, p. 31 (1982)). dPP-HV in the eye wiping test was comparable to RTX but in the other in vivo assays it was 2-4 orders of magnitude less potent. Since in the eye-wiping test RTX - perhaps due to its pharmacokinetics—was orders of magnitude less active than in the other assays for biological activity (Szallasi et al., Neuroscience, (in press, 1989)), the comparison of RTX and dPP-HV potencies by systemic administration may give the better estimate of affinity for the putative RTX receptor. It may be concluded that dPP-HV is more active than capsaicin and less active than RTX. The differences in the relative potencies of dPP-HV for desensitization in the eye-wiping and the Evan's blue extravasation assays are not very surprising, since previously 100-fold differences have been found in the relative potencies of RTX in the same assays as well (Szallasi et al., Neuroscience, (in press- 1989)).

The Weak potency of dPP-HV in inducing hypothermia is of particular interest since RTX was found to be more potent for inducing hypothermia than for desensitization of Evan's blue extravasation (Szallasi et al, Neuroscience, (in press, 1989)). This finding raises the possibility that homovanillyl-diterpene derivatives may afford a family of differential probes for different RTX-receptor subclasses. In any case, further investigation will be required to distinguish between factors affecting systemic distribution and intrinsic target affinity.

Mez-HV, in contrast to dPP-HV, was of very low potency as an RTX analog. It possessed only very weak pungency in the eye-wiping test, and it was inactive in RTX-like doses in the desensitization assays. These results suggests that the putative RTX-receptor was high selectivity for the nature of the diterpene moiety.

The following example further illustrates the composition of the present invention and will enable others skilled in the art to understand the invention more completely. It is understood that the invention is not limited to the Examples below.

EXAMPLE 5

2 mg of dPP-HV as the active ingredient is combined with 187 mg of microcrystalline cellulose as a carrier, 9 mg of stearic acid and 2 mg of colloidal silica. These materials are pressed to form a tablet.

EXAMPLE 6

A tablet is first formulated and prepared as in Example 5. The tablet is orally administered to a patient and 4-5 tablets represent a typical daily dosage.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A compound selected from the group consisting of formulas (I)-(IV):

wherein in formula (I), $R_2$ is

$R_3$ is H or $R_4$ is H or OH, $R_5$ is $CH_3$ or and wherein at least one of R', R" and R''' is an aromatic group and the remainder are $(CH_2)_{n'}$—$CH_3$ wherein n' is 0-14; said aromatic group having the formula:

wherein $R_6$-$R_{10}$ each independently represents OH, or H; and n is 0-10;

wherein in formula (II), $R_3$ is H, OH or

$R_4$ is H or and R', R" and R''' are as defined above;

wherein in formula (III), $R_3$, $R_4$, R', R" and R''' are the same as defined in formula (II); and wherein in formula (IV), $R_2$ is

$R_3$ is $CH_3$ or and $R_4$ is H or and R', R" and R''' are as defined above; wherein $R_1$ in formulas (I)–(IV) represents or with the proviso that in formula (II), R' is not

$R_3$ and $R_4$ are not H at the same time.

2. The compound of claim 1, which is 20-homovanillyl-mezerein.

3. The compound of claim 1, which is 20-homovanillyl-12-deoxyphorbol-13-phenylacetate.

4. The compound of claim 1, wherein the aromatic group of R', R" and R''' in formulas (I)–(IV) is wherein n is 0–10.

5. A method for desensitizing a subject animal, which comprises administering to said subject animal a therapeutically effective desensitizing amount of a compound selected from the group consisting of formulas (I)–(IV):

wherein in formula (I), $R_2$ is

$R_3$ is H or $R_4$ is H or OH, $R_5$ is $CH_3$ or and wherein at least one of R', R" and R''' is an aromatic group and the remainder are $(CH_2)_{n'}$—$CH_3$ wherein n' is 0–14, said aromatic group having the formula:

wherein $R_6-R_{10}$ each independently represents OH, $OCH_3$ or H; and n is 0–10;

wherein $R_1$ is homovanillic acid or an analog thereof possessing a pattern of substitution which would confer capsaicin-like activity were it in a capsaicin-like structure;

(II)

wherein in formula (II), $R_3$ is H, OH or

$R_4$ is H or and $R_1$, R', R" and R'" are as defined above;

(III)

wherein in formula (III), $R_1$, $R_3$, $R_4$, R', R" and R'" are the same as defined in formula (II); and (IV)

wherein in formula (IV), $R_2$ is $R_3$ is $CH_3$ or and $R_4$ is H or $$\overset{O}{\underset{\|}{OCR'''}},$$

and $R_1$, R', R" and R'" are as defined above, for desensitizing the subject to neurogenic inflammation, to chemically and thermally induced pain, to responses involving sensory afferent pathways sensitive to capsaicin and to responses involving the hypothalamic temperature control region, with the proviso that said compound is not resiniferatoxin.

6. The method of claim 5, wherein the compound is selected from the group consisting of tinyatoxin, 20-homovanillyl-mezerein and 20-homovanillyl-12-deoxyphorbol-13-phenylacetate.

7. The method of claim 5, wherein said compound is administered topically, subcutaneously, intraperitoneally, intravenously, or orally.

8. The method of claim 5, wherein said compound is administered in the range of $1 \times 10^{-5}$ mg/kg to 10 mg/kg to the subject.

9. The method of claim 5, wherein the subject is a mammal.

10. The method of claim 9, wherein the subject mammal is a mouse, rat, domestic animal, or human.

11. The method of claim 10, wherein the domestic animal is a dog, cat, horse, cow, pig, goat or sheep.

12. The method of claim 7, wherein the compound is administered by single or multiple application.

13. A composition comprising a therapeutically effective amount of the compound of claim 1 for desensitizing the subject to neurogenic inflammation, to chemically and thermally induced pain, to responses involving sensory afferent pathways sensitive to capsaicin and to responses involving the hypothalamic temperature control region, and a pharmaceutically acceptable carrier therefor.

14. The composition of claim 13, which comprises 0.0001 to 10% by weight of said compound.

15. The method of claim 5, wherein $R_1$ is homovanillic acid.

16. The method of claim 5, wherein $R_1$ is

17. The method of claim 5, wherein said compound is tinyatoxin.

18. A method for desensitizing a subject animal, which comprises administering to said subject animal a therapeutically effective desensitizing amount of a compound of claim 1 for desensitizing the subject to neurogenic inflammation, to chemically and thermally induced pain, to responses involving sensory afferent pathways sensitive to capsaicin and to responses involving the hypothalamic temperature control region.

* * * * *

UNITED STATES PATENT AND TRADEMARK OFFICE
Certificate

Patent No. 5,021,450                                              Patented: June 4, 1991

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of the patent is: Peter M. Blumberg, Frederick, MD and Arpad Szallasi, Rome, Italy.

Signed and Sealed this Thirteenth Day of March, 2001.

RICHARD L. RAYMOND
*Primary Examiner*
Art Unit 1624